United States Patent
Kanazawa

(10) Patent No.: US 7,354,398 B2
(45) Date of Patent: Apr. 8, 2008

(54) CAPSULE-TYPE DEVICE AND CAPSULE-TYPE DEVICE CONTROLLING SYSTEM

(75) Inventor: Masafumi Kanazawa, Tokyo (JP)

(73) Assignee: PENTAX Corporation, Tokyo (JP)

( * ) Notice: Subject to any disclaimer, the term of this patent is extended or adjusted under 35 U.S.C. 154(b) by 455 days.

(21) Appl. No.: 10/892,166

(22) Filed: Jul. 16, 2004

(65) Prior Publication Data

US 2005/0064815 A1    Mar. 24, 2005

(30) Foreign Application Priority Data

Jul. 18, 2003    (JP) ............................. 2003-199243

(51) Int. Cl.
*A61B 1/04*   (2006.01)
*A61B 1/05*   (2006.01)

(52) U.S. Cl. .................. 600/109; 600/117; 600/473; 600/424; 600/130

(58) Field of Classification Search ................ 600/424, 600/117, 118, 473, 407, 109, 130, 160
See application file for complete search history.

(56) References Cited

U.S. PATENT DOCUMENTS

| | | | |
|---|---|---|---|
| 5,558,091 A * | 9/1996 | Acker et al. ................. 600/424 |
| 5,729,129 A * | 3/1998 | Acker .................... 324/207.12 |
| 6,201,387 B1 * | 3/2001 | Govari .................. 324/207.17 |
| 6,233,476 B1 * | 5/2001 | Strommer et al. .......... 600/424 |
| 6,792,303 B2 * | 9/2004 | Taimisto ..................... 600/424 |
| 2002/0165448 A1 * | 11/2002 | Ben-Haim et al. .......... 600/424 |
| 2003/0120150 A1 * | 6/2003 | Govari ........................ 600/424 |
| 2003/0160721 A1 * | 8/2003 | Gilboa et al. ............... 342/450 |
| 2004/0138552 A1 * | 7/2004 | Harel et al. ................. 600/407 |
| 2005/0171427 A1 * | 8/2005 | Nevo et al. ................. 600/424 |
| 2005/0228259 A1 * | 10/2005 | Glukhovsky et al. ....... 600/407 |

FOREIGN PATENT DOCUMENTS

JP    224551    8/2001

* cited by examiner

*Primary Examiner*—John P. Leubecker
(74) *Attorney, Agent, or Firm*—Greenblum & Bernstein, P.L.C.

(57) ABSTRACT

There is provided a capsule-type device, which is provided with a power generator that generates power by receiving at least one of a time-varying electric field and a time-varying magnetic field, and a casing that surrounds the power generator. The power generator includes a plurality of receiving elements having different directionalities with regard to the at least one of the time-varying electric field and the time-varying magnetic field.

21 Claims, 17 Drawing Sheets

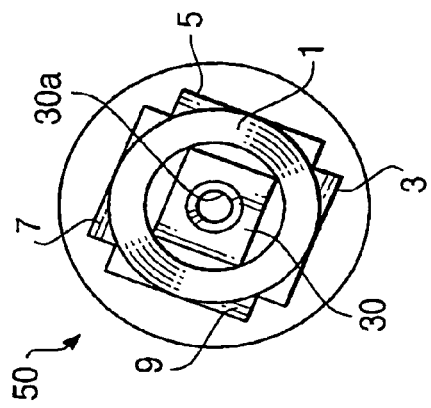
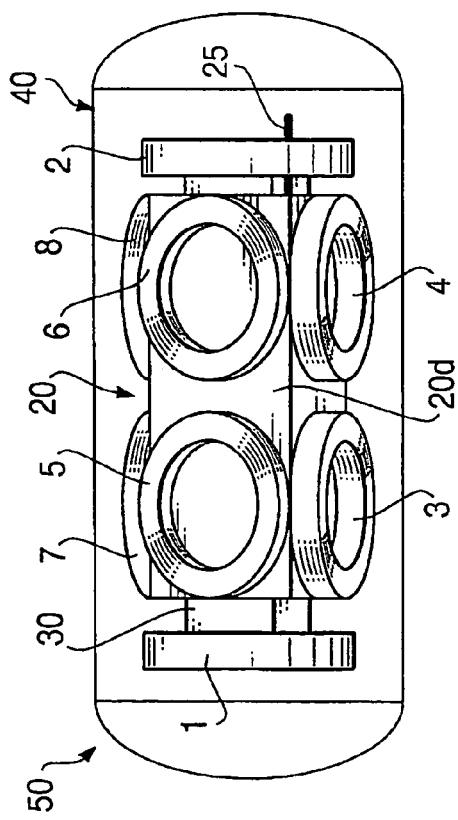
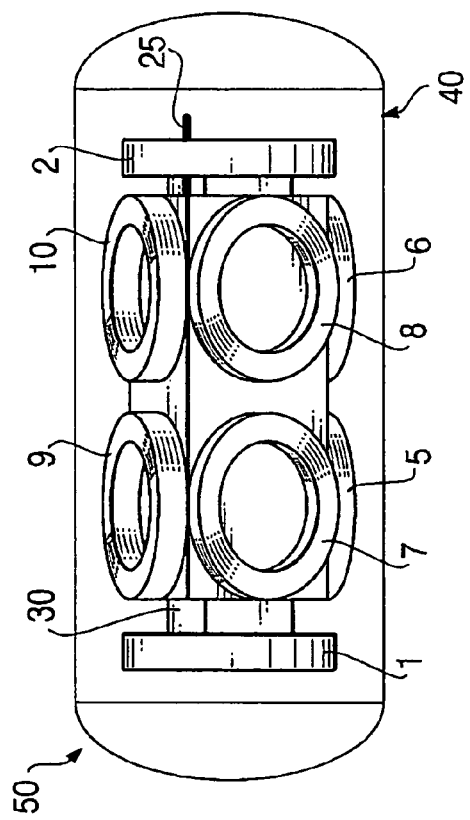
FIG.2C
FIG.2A
FIG.2B

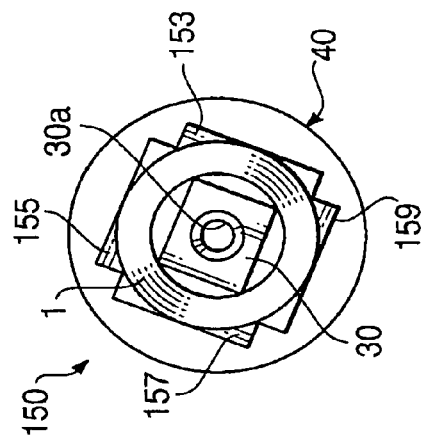
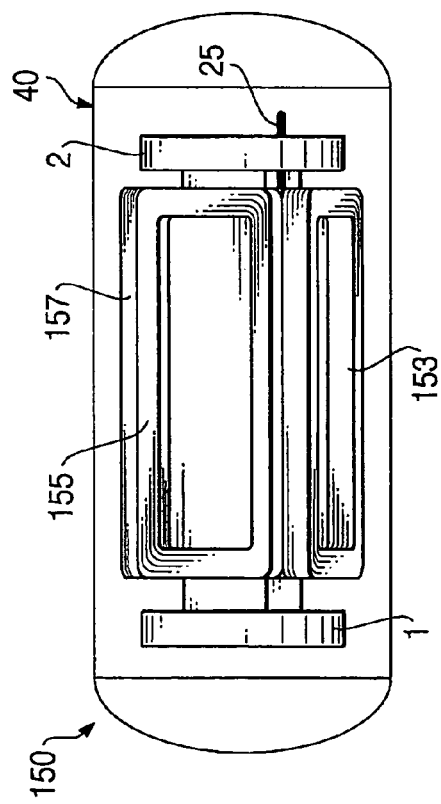
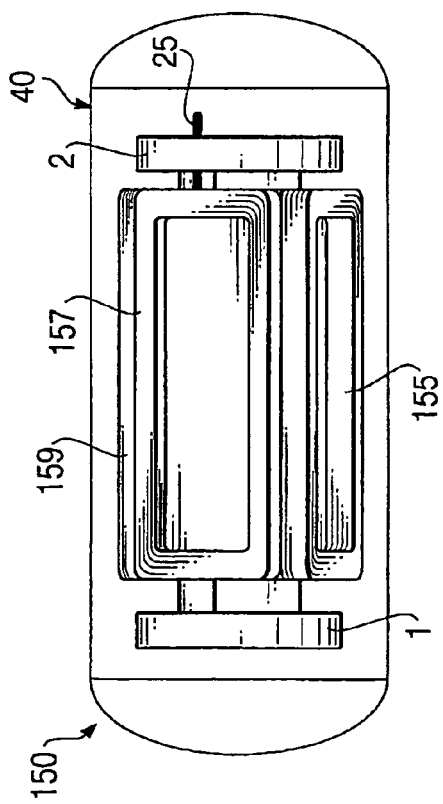

CAPSULE-TYPE DEVICE AND CAPSULE-TYPE DEVICE CONTROLLING SYSTEM

BACKGROUND OF THE INVENTION

The present invention relates to a capsule-type device which is capable of generating power, for example, by receiving a time-varying magnetic field generated by an external power source. The present invention further relates to a controlling system for such a capsule-type device.

Electronic endoscope systems for examining an internal body of a patient have been widely used. In general, such an electronic endoscope system includes an electronic endoscope which is inserted into the internal body of the patient, and a processor to which the electronic endoscope is attached. The electronic endoscope has an imaging device such as a CCD (charge-coupled device) at its tip portion to convert an image formed thereon by an objective lens to an image signal. The image signal is transmitted from the electronic endoscope to the processor to process the image signal. The image of a part of the internal body of the patient is thus obtained.

When an endoscopic examination is conducted for examining a digestive tube of the patient, an insertion tube portion of the electronic endoscope has to be inserted into the digestion tube of the patient. That is, the patient needs to swallow the insertion tube of the electronic endoscope, which causes pain to the patient.

Recently, capsule-type endoscopes have been proposed. The use of the capsule-type endoscope relieves the patient of the pain caused when the patient swallows the insertion tube of the electronic endoscope. The capsule-type endoscope has a small size so that the patient can swallow it. Further, the capsule-type endoscope is configured to obtain an image of the internal body of the patient and to transmit the image as a radio signal.

Japanese Patent Provisional Publication No. 2001-224551 discloses such a capsule-type endoscope. FIG. 15 is a block diagram of a capsule-type endoscope 100 disclosed in the publication. The capsule-type endoscope 100 is used as a part of a capsule-type endoscope system. The capsule-type endoscope system includes a processor and an external power source (not shown in FIG. 15), which are located outside of the patient body.

The capsule-type endoscope 100 is capable of communicating with the processor by a radio signal. The processor is used to remotely control the capsule-type endoscope 100 and to process an image signal transmitted from the capsule-type endoscope 100. The external power source supplies the capsule-type endoscope 100 with power by generating a time-varying magnetic field.

As shown in FIG. 15, the capsule-type endoscope 100 includes an objective lens system 101, an image sensor 102, a signal processing circuit 103, a transmitter 104 and a coil 105, which are enclosed by a casing 107. The objective lens system 101 forms an image of an object on the image sensor 102. The image sensor 102 converts the image formed thereon to an electric signal. The electric signal generated by the image sensor 102 is processed by the signal processing circuit 103 to generate an image signal. Then, the image signal generated by the signal processing circuit 103 is transmitted through the transmitter 104 as the radio signal.

The coil 105 is located on a portion of an internal surface of the casing 107 (i.e., (on the inside bottom surface of the casing in FIG. 15)) so that the coil 105 generates power by intersecting with a magnetic flux generated by the external power source.

When the capsule-type endoscope 100 is swallowed by the patient, the coil 105 of the capsule-type endoscope 100 receives the time-varying magnetic flux generated by the external power source and then generates power. The power generated by the coil 105 is supplied to various circuits including the image sensor 102, the processing circuit 103 and the transmitter 104 in the capsule-type endoscope 100.

Other types of the capsule-type device, configured to generate power by receiving a time-varying magnetic field and used to observe the internal body of the patient, are also proposed.

One of problems of the conventional capsule-type devices described above is that there is a case where electromotive force is reduced depending on an angle formed between the coil 105 and the magnetic flux generated by the external power source because the coil 105 is formed only on the portion of the internal surface of the casing 107.

Another problem of the conventional capsule-type device is that the capsule-type device existing in the patient body easily changes its attitude (i.e., orientation), for example, by peristalsis of the digestion tube of the patient. Therefore, it is very difficult to detect the attitude of the capsule-type device.

SUMMARY OF THE INVENTION

The present invention is advantageous in that it provides a capsule-type device and a controlling system of the capsule-type device capable of steadily generating power regardless of an attitude of the capsule type device.

According to an aspect of the invention, there is provided a capsule-type device, which is provided with a power generator that generates power by receiving at least one of a time-varying electric field and a time-varying magnetic field, and a casing that surrounds the power generator. The power generator includes a plurality of receiving elements having different directionalities with regard to the at least one of the time-varying electric field and the time-varying magnetic field.

With this configuration, the capsule-type device can constantly and steadily generate the power regardless of an attitude thereof.

Optionally, the plurality of receiving elements may be located so that the plurality of receiving elements have the different directionalities.

Still optionally, the plurality of receiving elements may be located on planes having different orientations.

In a particular case, the plurality of receiving elements may have the same electric and/or magnetic characteristic.

Optionally, the plurality of receiving elements may be located on side surfaces of a rectangular prism shape.

Still optionally, the capsule-type device may include a comparing system that makes a comparison among outputs of at least three receiving elements of the plurality of receiving elements so that an angular relationship between the at least three receiving elements with respect to an outside power source generating the at least one of the time-varying electric field and the time-varying magnetic field is detected. The at least three receiving elements are located perpendicularly to each other and are located adjacent to each other. Further, the capsule-type device includes a transmitter that transmits a result of the comparison performed by the comparing system by a radio signal.

In a particular case, the capsule-type device may include a comparing system that makes a comparison among outputs of at least two receiving elements of the plurality of receiving elements so that positional relationship between the at least two receiving elements with respect to an outside power source generating the at least one of the time-varying electric field and the time-varying magnetic field is detected. The at least two receiving elements are located in parallel with each other and are located coaxially with respect to each other. Further, the capsule-type device includes a transmitter that transmits a result of the comparison performed by the comparing system by a radio signal.

Still optionally, the plurality of receiving elements may be located on three of the side surfaces of the rectangular prism shape.

In a particular case, the plurality of receiving elements may be located on all of the side surfaces the rectangular prism shape.

In a particular case, the capsule-type device may include a transmitter that transmits information concerning outputs of the plurality of receiving elements by a radio signal.

In a particular case, the capsule-type device may include a comparing system that makes a comparison among outputs of the plurality of receiving elements to determine an attitude of the capsule-type device, and a transmitter that transmits the determined attitude of the capsule-type device by a radio signal.

In a particular case, the capsule-type device may include at least one sensor used for obtaining information concerning an internal body of a subject when the capsule-type device is in the internal body of the subject, and a transmitter that transmits the information, obtained by the at least one sensor, by a radio signal.

In a particular case, the capsule-type device may include an objective lens system that forms an image of an object, an image pickup device that converts the image formed thereon by the objective lens system to an image signal, and a transmitter that transmits the image signal, generated by the image pickup device, by a radio signal.

Optionally, the plurality of receiving elements may have coils respectively located on planes having different orientations, and the coils may include a coil located to cross an optical path of the objective lens system. The optical path passes through an opening of the coil.

In a particular case, the plurality of receiving elements may include coils.

Optionally, the coils may be formed as vortical patterns on a printed circuit board.

In a particular case, the capsule-type device may include a rechargeable battery that is used to temporarily accumulate the power generated by the power generator.

In a particular case, the plurality of receiving elements may generate power by receiving a microwave.

According to another aspect of the invention, there is provided a capsule-type device controlling system, which is provided with an outside power source that generates a time-varying magnetic field, and a capsule-type device including a power generator that generates power by receiving the time-varying magnetic field to supply the power to internal components of the capsule-type device. In this structure, the power generator includes a plurality of coils located on at least three of side surfaces of a rectangular prism shape.

With this configuration, the capsule-type device can constantly and steadily generate the power regardless of an attitude thereof.

Optionally, the capsule-type device may include an objective lens system that forms an image of an object, an image pickup device that converts the image formed thereon by the objective lens system to an image signal, and a transmitter that transmits the image signal, generated by the image pickup device, by a radio signal.

In a particular case, the capsule-type device may include a transmitter that transmits information concerning outputs of the plurality of coils by a radio signal.

Optionally, the capsule-type device controlling system may include a processor having a receiver that receives the radio signal transmitted by the transmitter of the capsule-type device. The processor determines an attitude of the capsule-type device with respect to the outside power source based on the received information.

In a particular case, the capsule-type device may include a comparing system that makes a comparison among outputs of the plurality of coils to determine an attitude of the capsule-type device, and a transmitter that transmits the determined attitude of the capsule-type device by a radio signal.

BRIEF DESCRIPTION OF THE ACCOMPANYING DRAWINGS

FIG. 2A is a side view of the capsule-type endoscope shown in FIG. 1 viewed along one direction;

FIG. 2B is a side view of the capsule-type endoscope shown in FIG. 1 viewed along another direction;

FIG. 2C is a front view of the capsule-type endoscope shown in FIG. 1;

Figure 5:
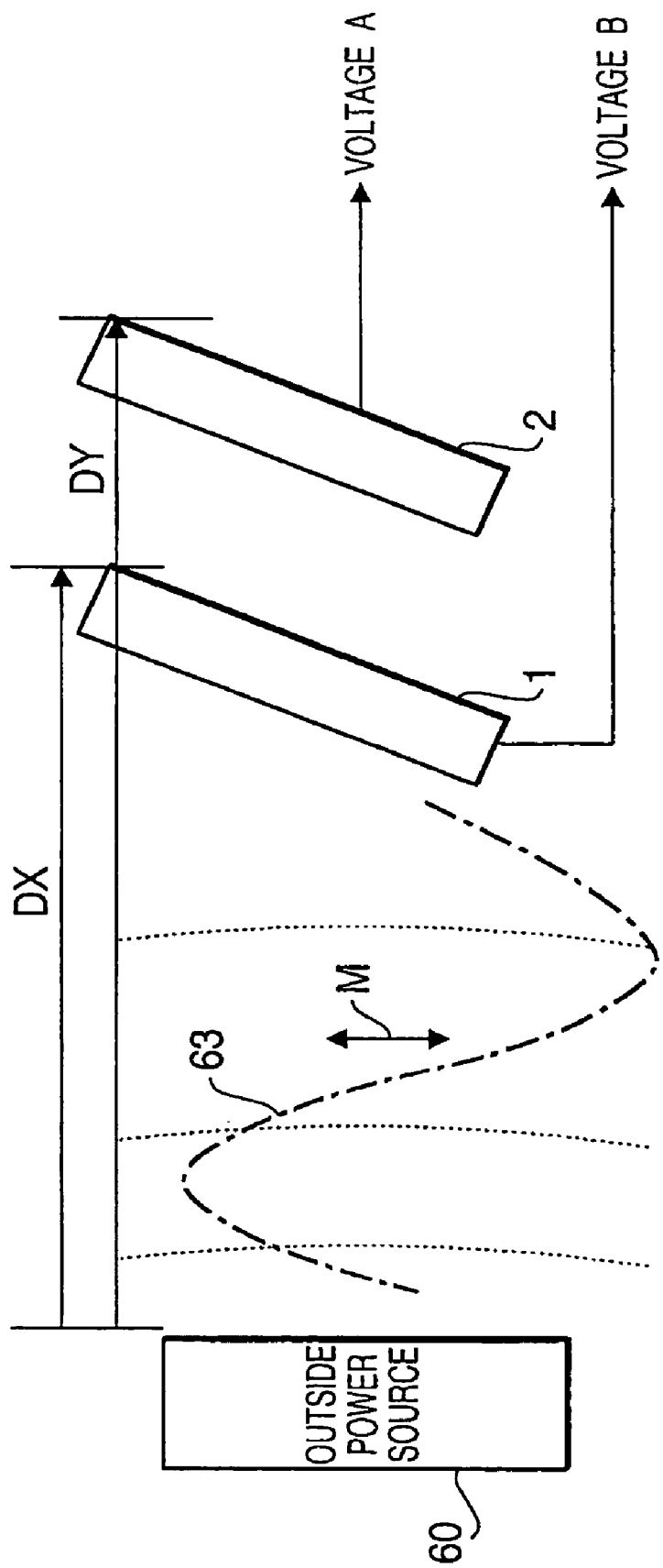
Figure 6:
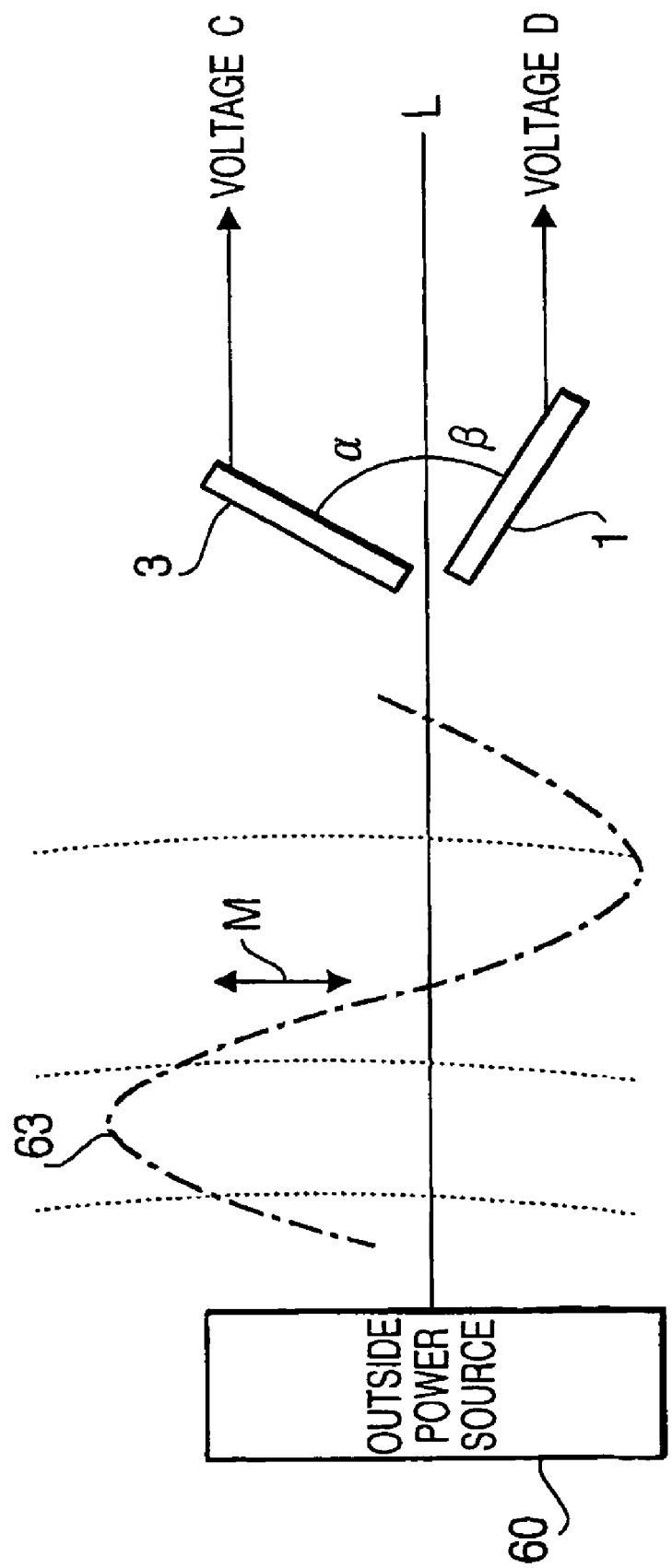
Figure 7:
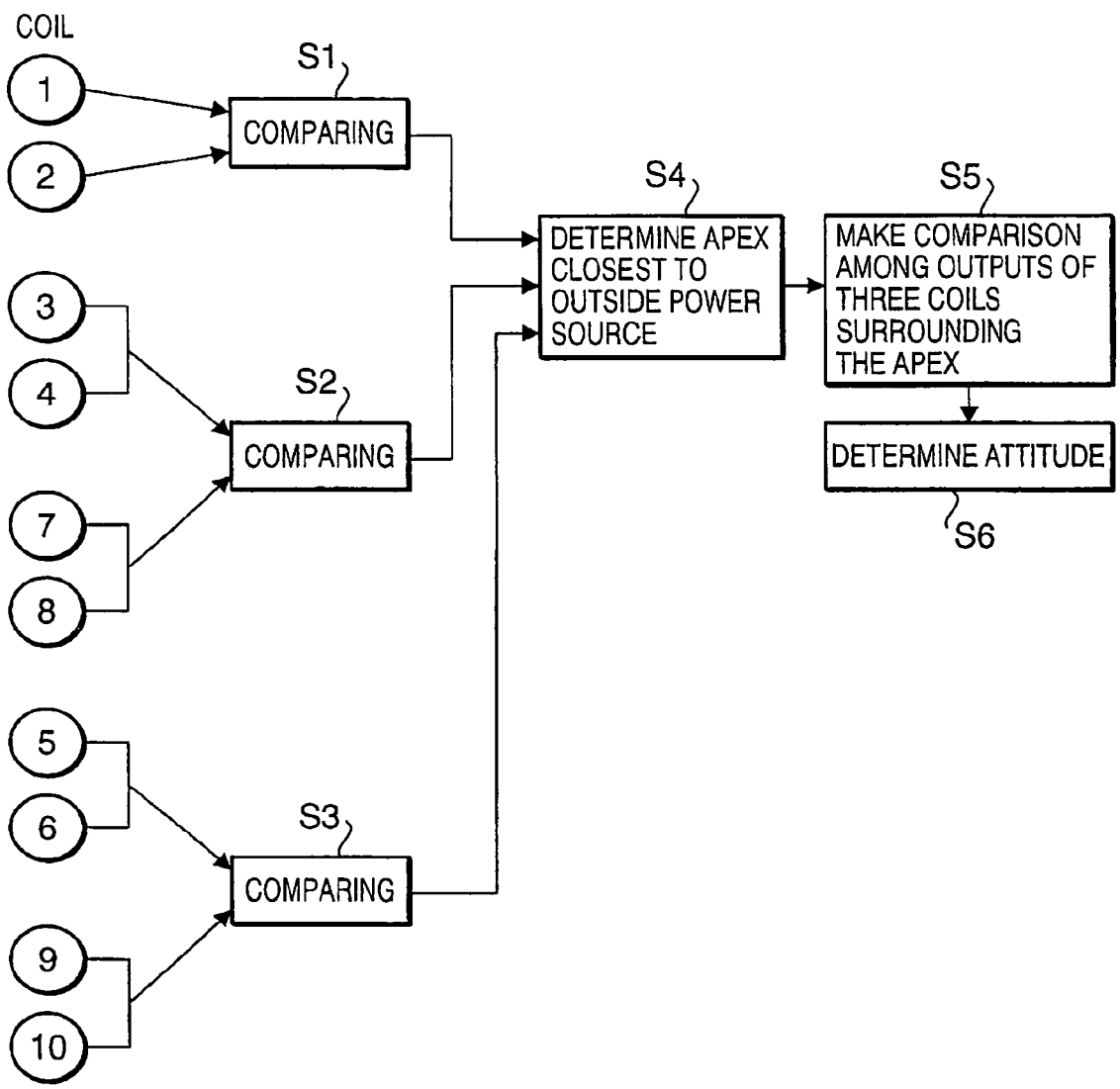
Figure 8:
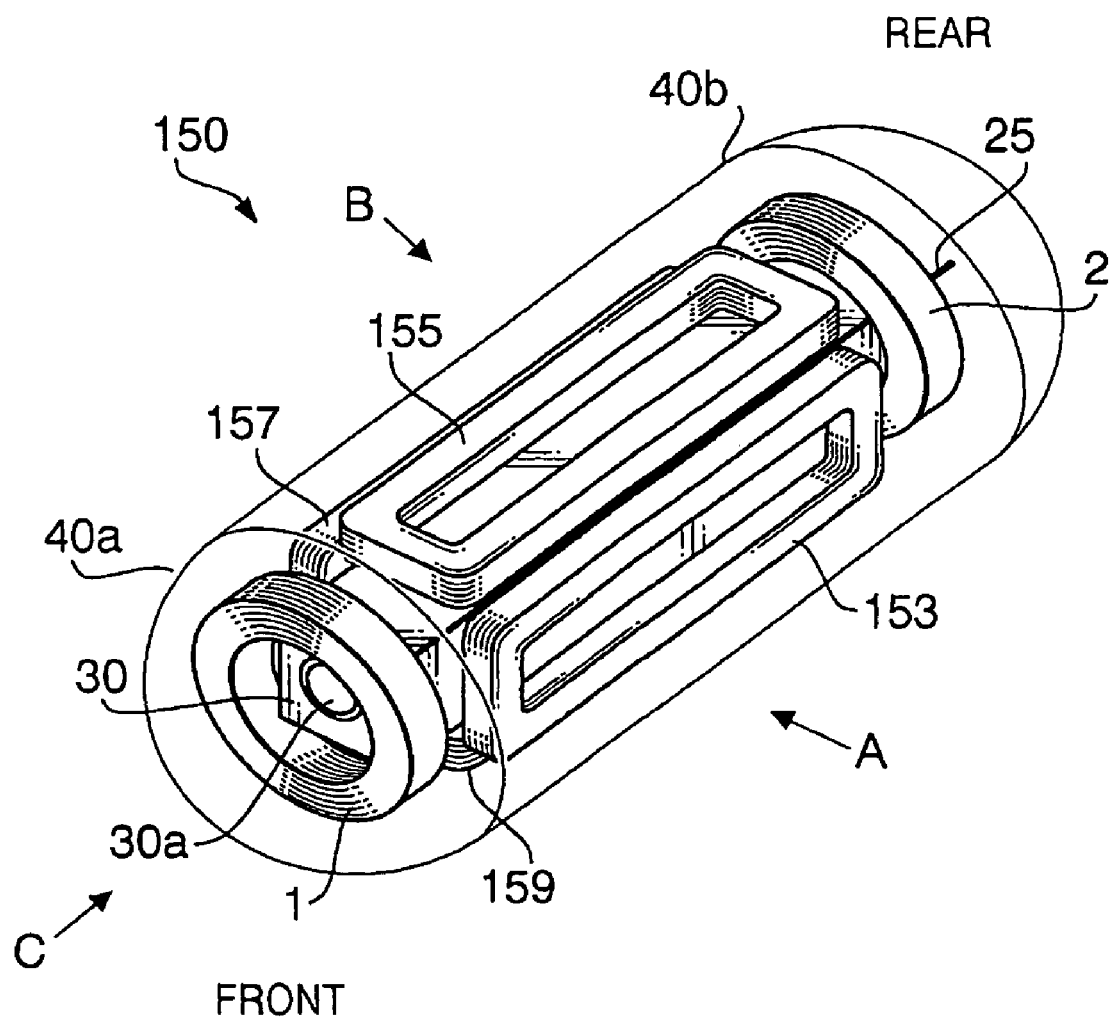
Figure 10:
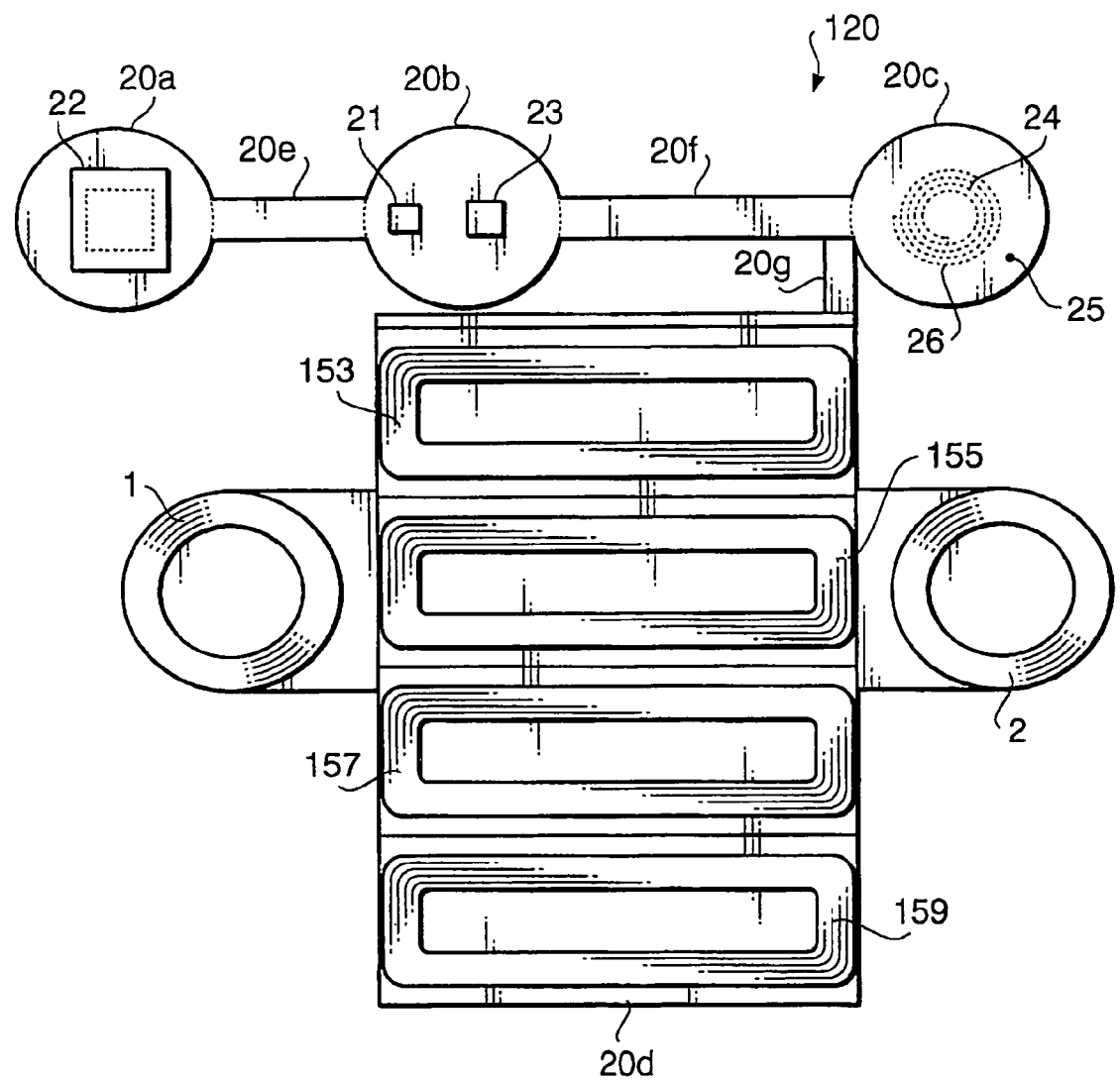
Figure 11:
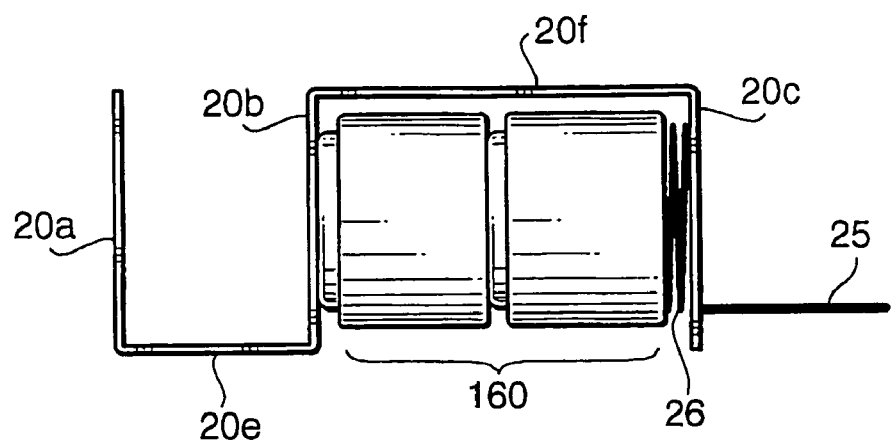
Figure 12:
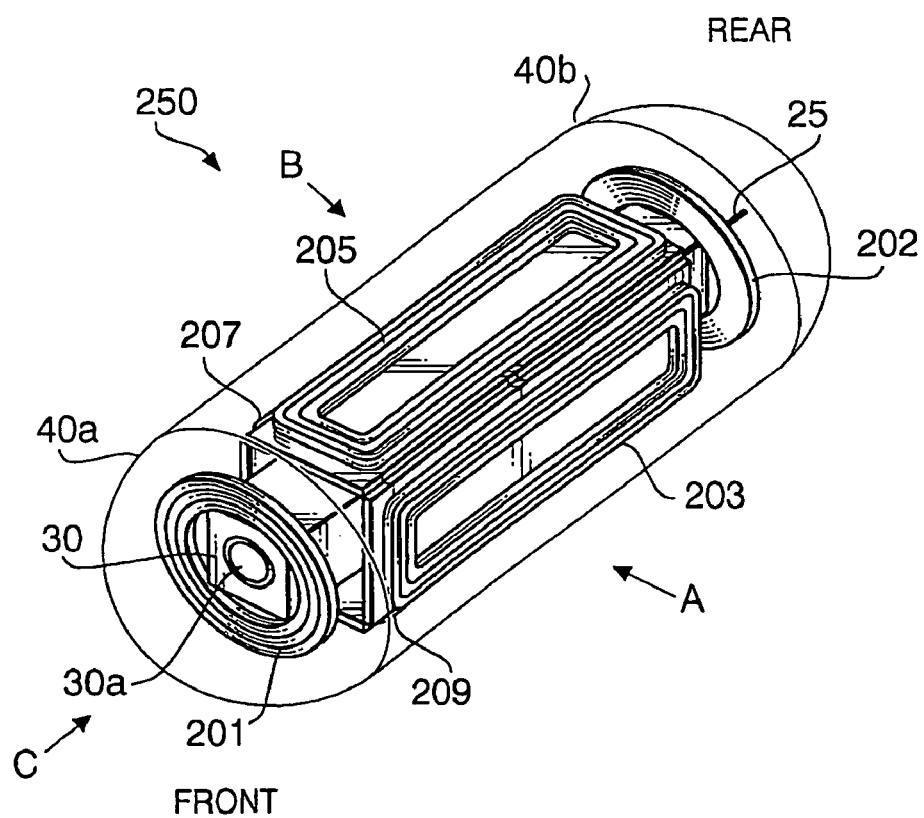
Figure 13C:
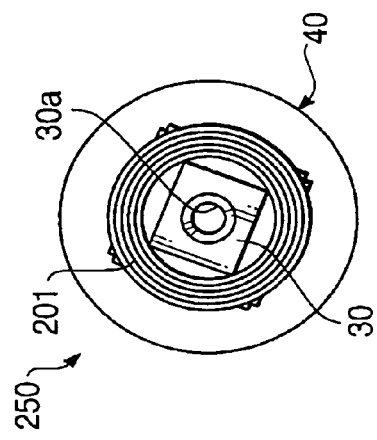
Figure 13A:
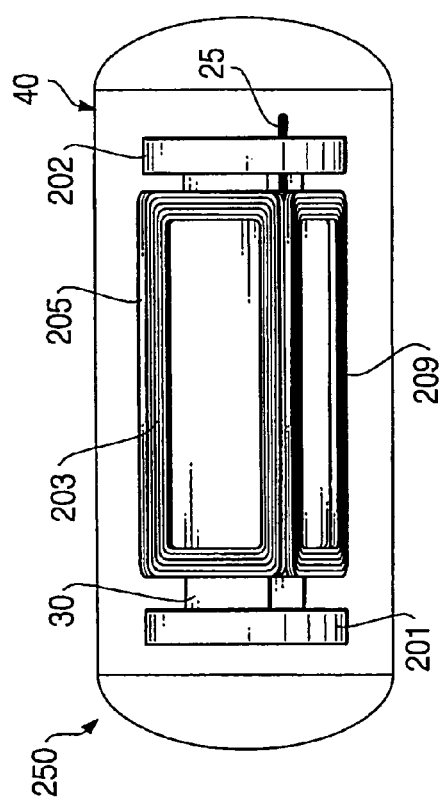
Figure 13B:
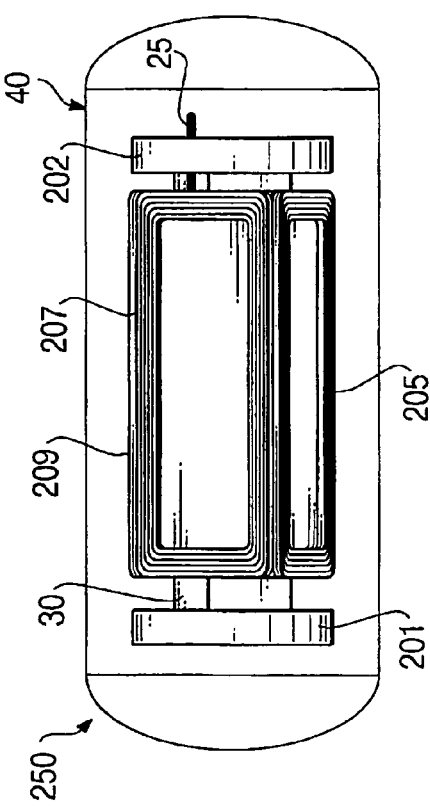
Figure 14:
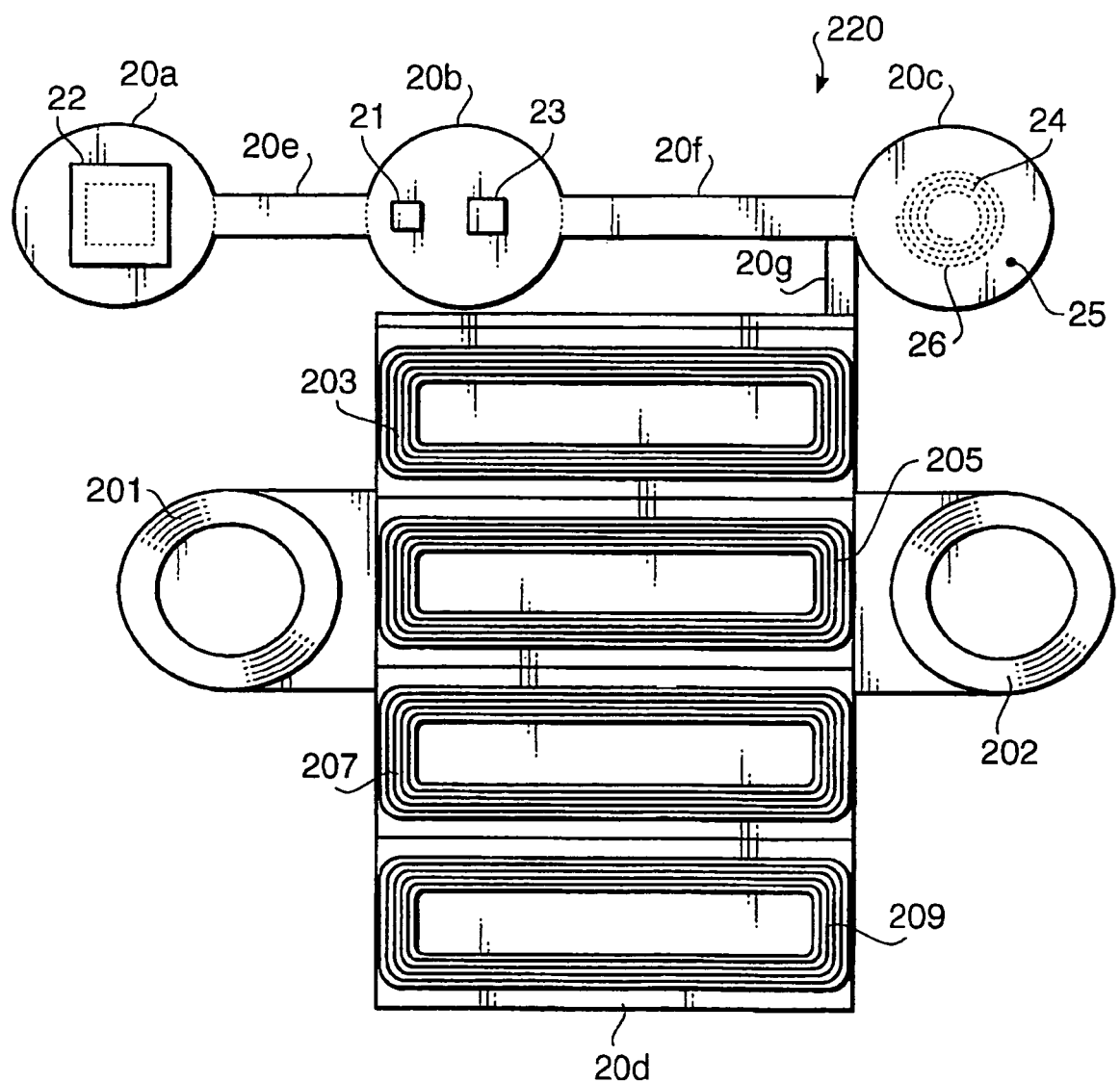
Figure 15:
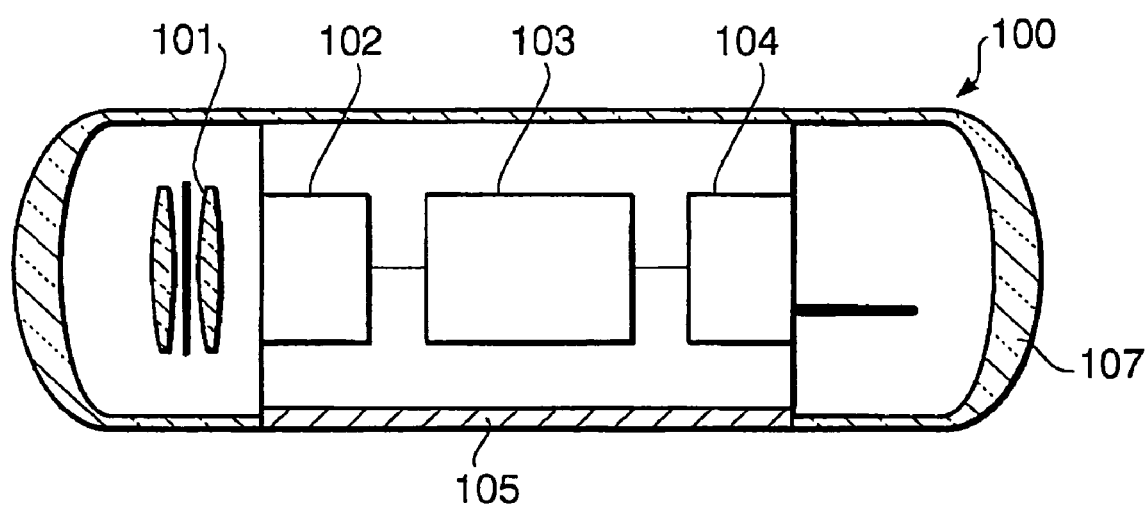
Figure 16:
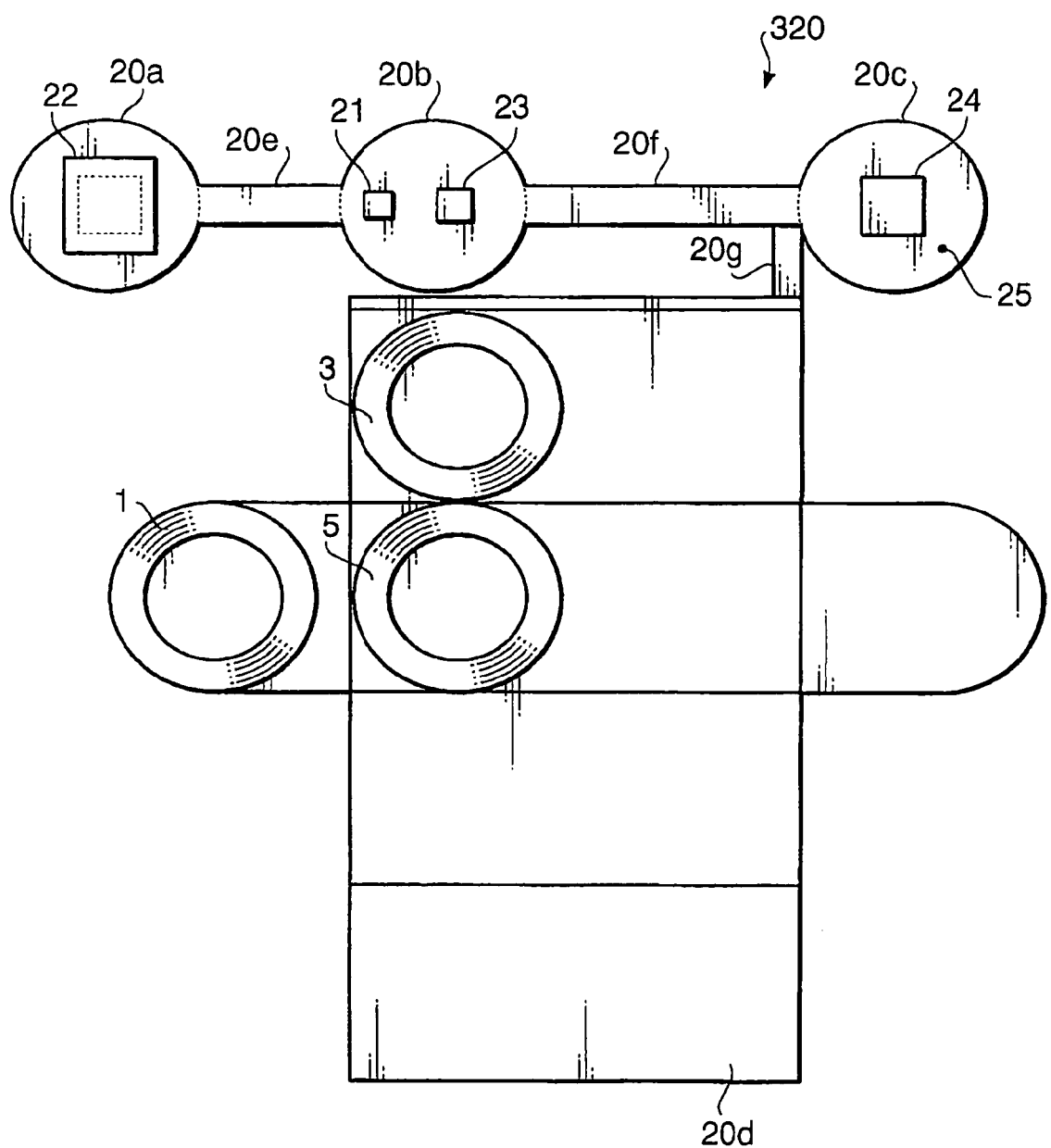
Figure 17A:
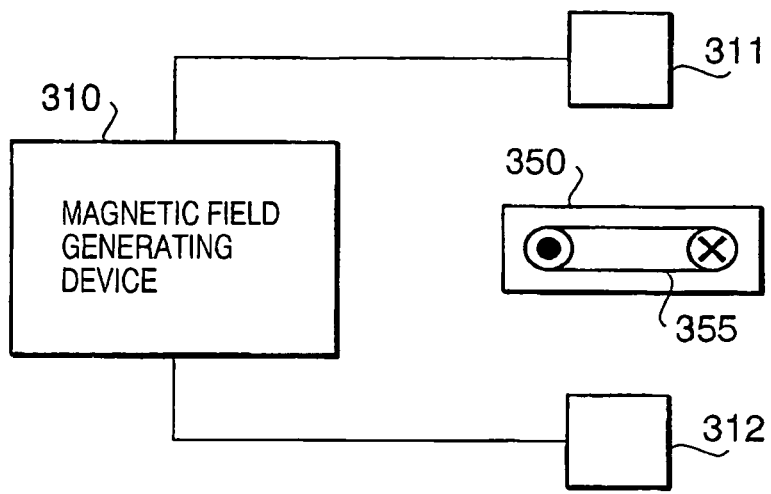
Figure 17B:
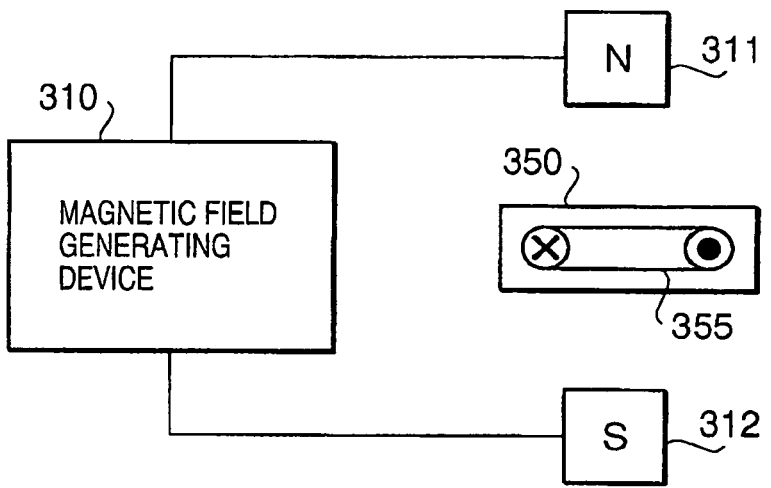
Figure 18:
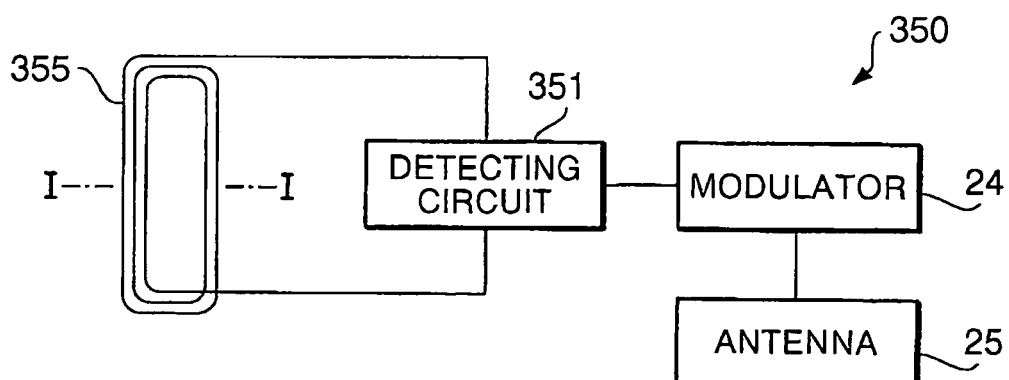
Figure 19:
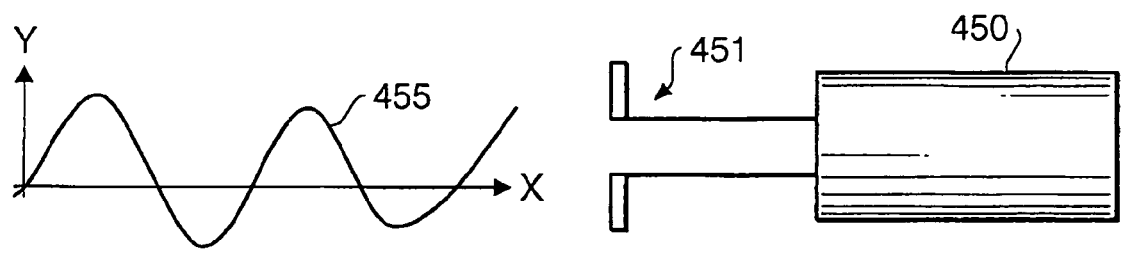
Figure 20:
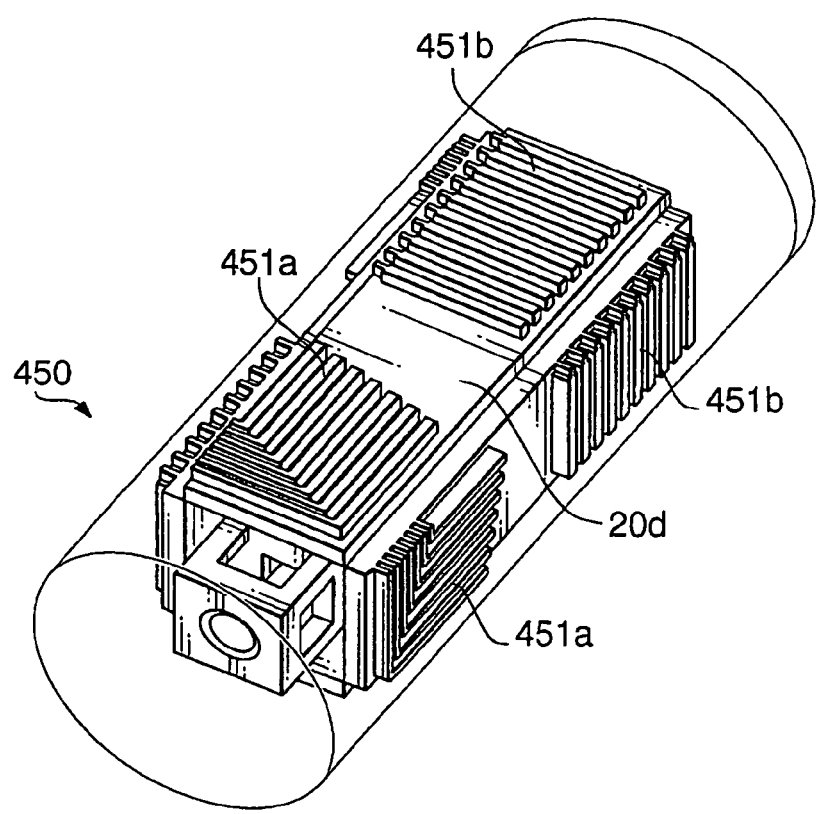

FIG. 5 schematically shows two coils which are arranged in the capsule-type endoscope so that positional relationship thereof is calculated;

FIG. 6 schematically shows two coils which are arranged in the capsule-type endoscope so that an angular relationship thereof is calculated;

FIG. 7 shows a flow of operation for determining an attitude of the capsule-type endoscope executed by a comparing circuit of the capsule-type endoscope;

FIG. 8 is a perspective view of a capsule-type endoscope according to a second embodiment of the invention;

FIG. 9A is a side view of the capsule-type endoscope shown in FIG. 8 viewed along one direction;

FIG. 9B is a side view of the capsule-type endoscope shown in FIG. 8 viewed along another direction;

FIG. 9C is a front view of the capsule-type endoscope shown in FIG. 8;

FIG. 10 is a developed view of a printed circuit board provided in the capsule-type endoscope shown in FIG. 8;

FIG. 11 shows a situation where a battery is accommodated in the capsule-type endoscope shown in FIG. 8:

FIG. 12 is a perspective view of a capsule-type endoscope according to a third embodiment of the invention;

FIG. 13A is a side view of the capsule-type endoscope shown in FIG. 12 viewed along one direction;

FIG. 13B is a side view of the capsule-type endoscope shown in FIG. 12 viewed along another direction;

FIG. 13C is a front view of the capsule-type endoscope shown in FIG. 12;

FIG. 14 is a developed view of a printed circuit board provided in the capsule-type endoscope shown in FIG. 12;

FIG. 15 is a block diagram of a conventional capsule-type endoscope;

FIG. 16 shows a printed circuit board of a capsule-type endoscope configured to have three coils located on three of side surfaces;

FIG. 17A is a block diagram of a magnetic field generating device illustrating a situation where the magnetic field generating device is turned on;

FIG. 17B is a block diagram of a magnetic field generating device illustrating a situation where the magnetic field generating device is turned off;

FIG. 18 is a block diagram of a capsule-type endoscope used together with the magnetic field generating device shown in FIGS. 17A and 17B;

FIG. 19 shows a capsule-type endoscope configured to generate power by receiving a time-varying electric field; and FIG. 20 shows an outward appearance of the capsule-type endoscope shown in FIG. 19.

DETAILED DESCRIPTION OF THE EMBODIMENTS

Hereinafter, embodiments according to the invention are described with reference to the accompanying drawings.

First Embodiment

Figure 1:
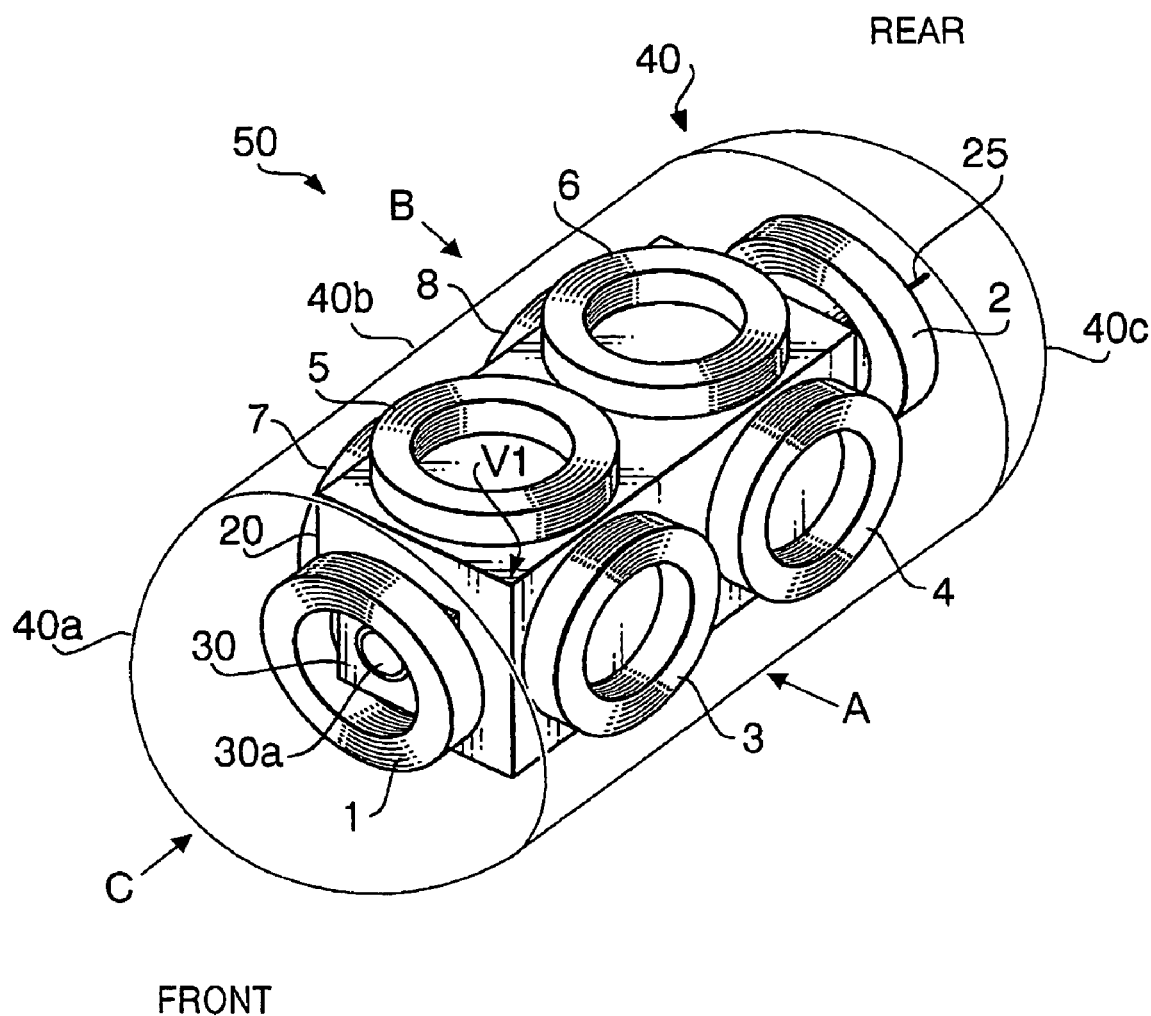
FIG. 1 is a perspective view of a capsule-type endoscope according to a first embodiment of the invention.

FIG. 1 is a perspective view of a capsule-type endoscope 50 according to a first embodiment of the invention. In the following explanation, the left side of the capsule-type endoscope 50 in FIG. 1 is defined as a front side, and a right side of the capsule-type endoscope 50 in FIG. 1 is defined as a rear side. The capsule-type endoscope 50 is used as a part of a capsule-type endoscope controlling system 90 (see FIG. 4).

FIG. 2A is a side view of the capsule-type endoscope 50 viewed along an arrow A shown in FIG. 1. FIG. 2B is a side view of the capsule-type endoscope 50 viewed along an arrow B shown in FIG. 1. FIG. 2C is a front view of the capsule-type endoscope 50 viewed along an arrow C shown in FIG. 1. As shown in FIGS. 1 and 2A-2C, the capsule-type endoscope 50 includes an image pickup unit 30, a printed circuit board 20, and coils 1-10, which are enclosed and protected by a casing 40. The printed circuit board 20 is folded to have a form of a rectangular prism.

The casing 40 includes a transparent cover 40a, a body portion 40b having a cylindrical form, and a tail portion 40c. The transparent cover 40a and the tail portion 40c have the same semispheric form. The entire casing 40 has a form of a so-called capsule and has a small size so that a patient can swallow it.

The transparent cover 40a is transparent and is made of acid-resistant material. The transparent cover 40a also has the function of providing an appropriate distance between an objective lens system 30a of the image pickup unit 30 and an object. The body portion 40b and the tail portion 40c are made of material which shields light and is resistant to acid (e.g., acid-resistant plastic). Is should be noted that although the body portion 40b is optically nontransparent, in FIGS. 1 and 2A-2C the body portion 40b is indicated as transparent material for convenience of explanation.

The image pickup unit 30 is located at the front side of the casing 40. The image pickup unit 30 has the objective lens system 30a and an image sensor 22 (see FIG. 3), which are enclosed by a casing having a form of a flat rectangular prism. The image pickup unit 30 is located on a front side surface of the printed circuit board 20 such that an optical axis of the objective lens system 30a coincides with a rotation axis of the transparent cover 40a.

When an outside power source 60 (see FIG. 4) applies a time-varying magnetic field to the capsule-type endoscope 50, electromotive force is generated in each of the coils 1-10 by electromagnetic induction. The power (i.e., current) generated by the coils 1-10 is supplied to various components provided in the capsule-type endoscope 50. The coils 1-10 have the same annular shape and have the same electric characteristic (i.e., the coils 1-10 have the same number of turns and the same diameter). Therefore, the coils 1-10 output the same power when they are in the same time-varying magnetic field.

The coils 1-10 are fixed on the printed circuit board 20. The coils 1 and 2 are located on the front and rear surfaces of the printed circuit board 20, respectively. The coils 3 and 4 are located at the front side and the rear side on one of side surfaces of the printed circuit board 20, respectively. The coils 5 and 6 are located at the front side and the rear side on one of side surfaces of the printed circuit board 20, respectively. The coils 7 and 8 are located at the front side and the rear side on one of side surfaces of the printed circuit board 20, respectively. The coils 9 and 10 are located at the front side and the rear side of one of side surfaces of the printed circuit board 20, respectively.

Figure 3:
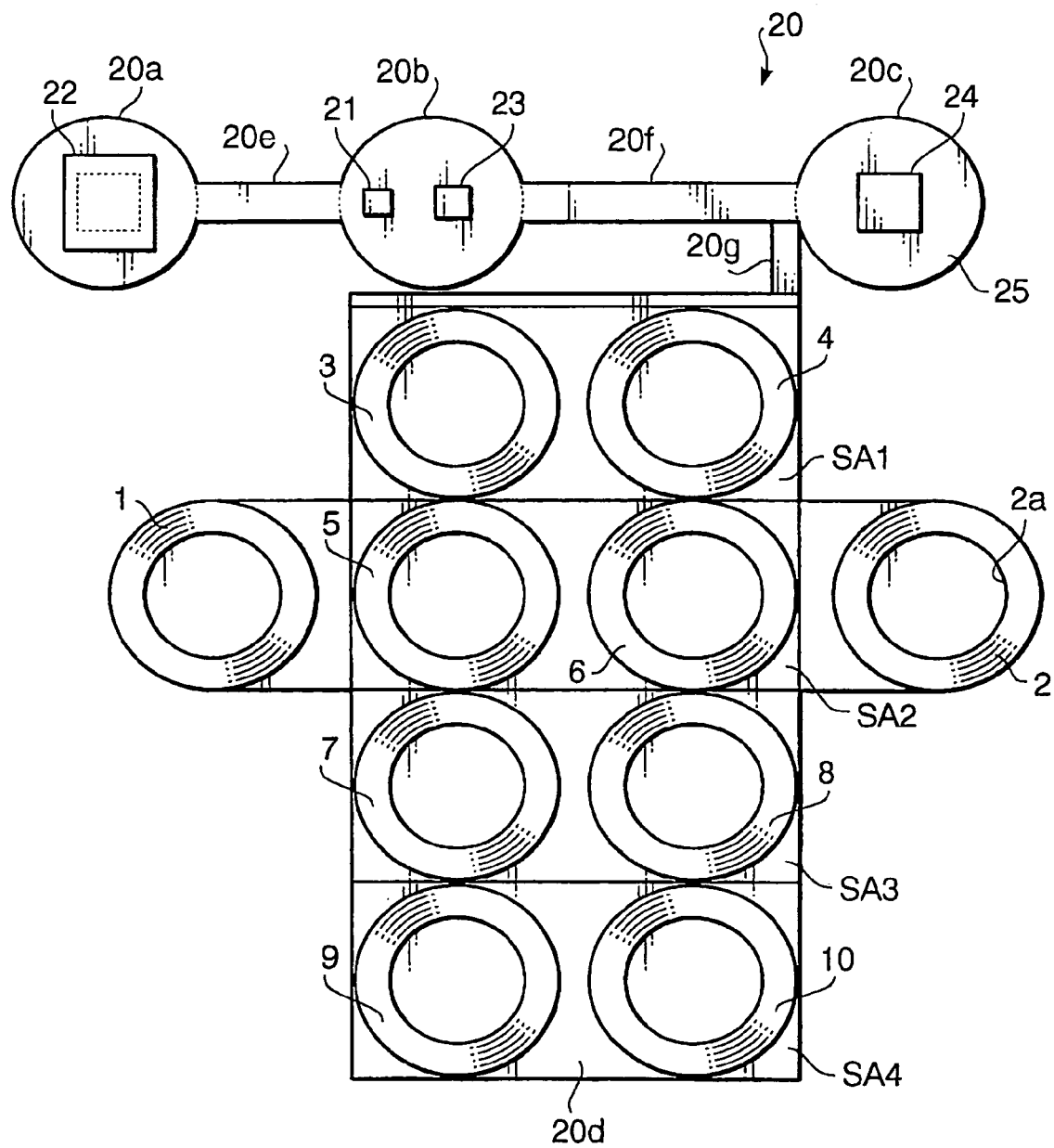
FIG. 3 is a developed view of a printed circuit board provided in the capsule-type endoscope.

FIG. 3 is a developed view of the printed circuit board 20 illustrating positional relationships of the coils 1-10. The printed circuit board 20 is formed by a flexible printed circuit board. As shown in FIG. 3, the printed circuit board 20 includes a front circular board 20a, an inside circular board 20b, a rear circular board 20c and a side board 20d, which are connected to each other by connecting boards 20e-20f. In the developed view of FIG. 3, the front, inside and rear circular boards 20a, 20b and 20c are arranged along a line parallel with longitudinal sides of the connecting boards 20e and 20f. The side board 20d has a rectangular form.

A connecting board 20g extends from a rear end portion of the connecting board 20f and is connected to an end portion of one of shorter sides of the side board 20d.

The front, inside and rear circular boards 20a, 20b and 20c have the same shape (i.e., the same radius). When the printed circuit board 20 is assembled and is mounted in the casing 40, the front, inside and rear circular boards 20a, 20b and 20c are folded at positions indicated by hashed lines in FIG. 3 such that the front, inside and rear circular boards 20a, 20b and 20c become parallel with each other and are located coaxially.

When the printed circuit board 20 is completely assembled and is mounted in the casing 40, the front, inside and rear circular boards 20a, 20b and 20c are located at the front side, an intermediate portion and the rear side of the capsule-type endoscope 50, respectively. Further, the side board 20d is folded at lines parallel with the shorter side thereof to have a form of a rectangular prism surrounding the front, inside and rear circular boards 20a, 20b and 20c.

On each of the circular boards 20a, 20b and 20c, circuits are provided. More specifically, on the front circuit board 20a, the image pickup unit 30 is located. On the inside circular board 20b, a comparing circuit 21 and a signal processing circuit 23 are located. On the rear circular board 20c, a modulator 24 and an antenna 25 are located. The circuits on the front, inside, and rear circular boards are supplied with power by the coils 1-10. Further, the printed circuit board 20 is provided with a light source (not shown) used for illuminating the object. The light source is also supplied with power by the coils 1-10.

As described in detail later, the comparing circuit 21 performs calculation based on outputs from the coils 1-10 to obtain an attitude of the capsule-type endoscope 50 in the internal body of the patient. The result of the calculation is then outputted form the comparing circuit 21 as an attitude signal.

The image sensor 22 converts the image formed thereon by the objective lens system 30*a* to an electric signal and transmits the electric signal to the signal processing circuit 23. The image sensor 22 is fixed in the image pickup unit 30 such that light from the object is converged onto a light receiving surface of the image sensor 22.

The signal processing circuit 23 performs predetermined processes for the electric signal from the image sensor 22 to generate an image signal. The predetermined processes include a white balance calibration, gamma correction and analog-to-digital conversion.

The modulator 23 has the function of modulating the attitude signal and the image signal. The modulator 24 also has the function as an amplifier. The signals modulated by the modulator 24 are transmitted as radio signals via the antenna 25. The radio signal transmitted from the antenna 25 is then received by a processor 70 (see FIG. 4) located outside of the patient body. The antenna 25 protrudes perpendicularly to the rear circular board 20*c* toward the rear side of the capsule-type endoscope 50.

As shown in FIG. 3, the coils 3-10 are mounted on the side board 20*d*. More specifically, four pairs of coils (a pair of coils 3 and 4, a pairs of coils 5 and 6, a pair of coils 7 and 8, and a pair of coils 9 and 10) are arranged in parallel with the longitudinal side of the side board 20. Lines connecting center points of adjacent ones of the coils 3-10 on the side board 20 (e.g., a line connecting center points of the coils 3 and 5 or the coils 3 and 4) is parallel with the shorter side or the longitudinal side of the side board 20.

The coils 1 and 2 are electrically connected to the side board 20*d* via electrodes located along longitudinal sides of the side board 20*d*, respectively. The coils 1 and 2 are respectively located on the front side and rear side of the capsule-type endoscope 50. When the printed circuit board 20 is completely assembled and accommodated in the casing 40, the coil 1 is positioned at the front side of the image pickup unit 30 such that the optical axis of the objective lens system 30*a* passes through a center point of the coil 1. Further, the coil 2 is located at the rear side in the casing 40 such that the antenna 25 passes through an opening 2*a* (see FIG. 3) of the coil 2.

Figure 4:
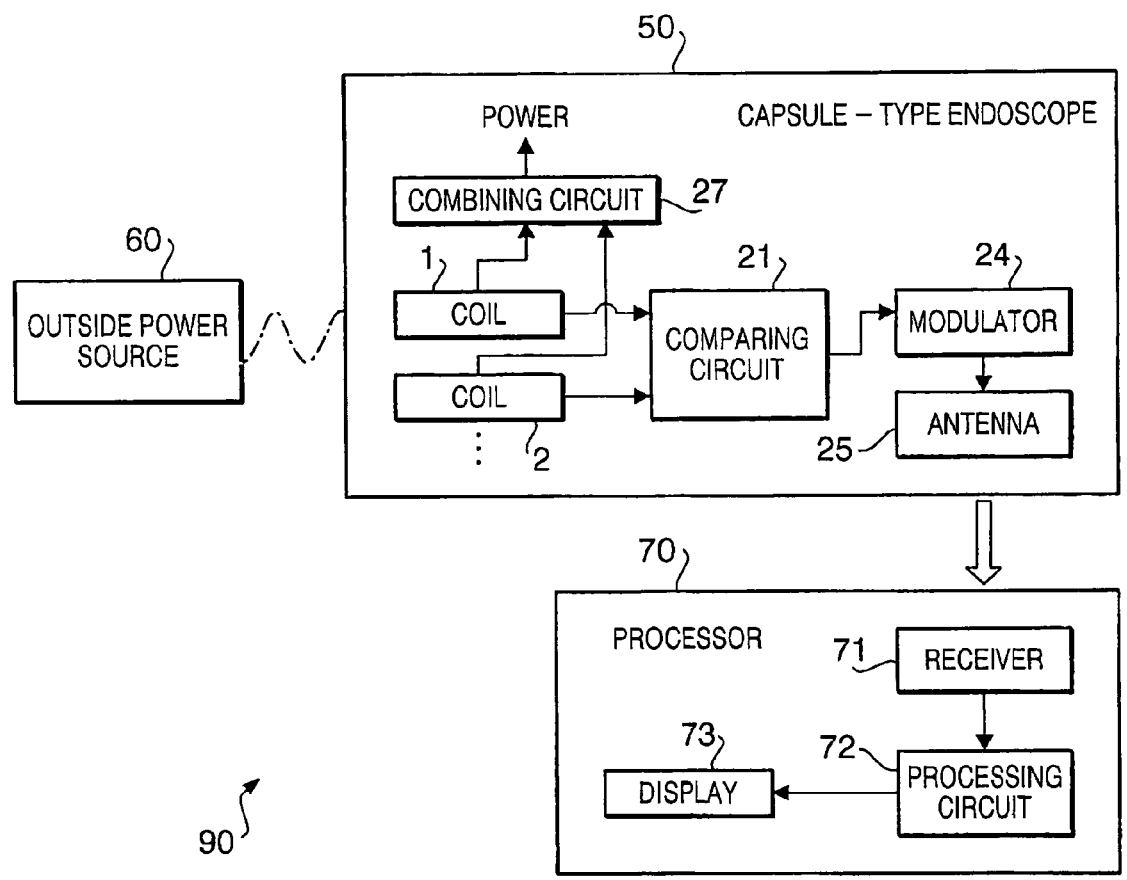
FIG. 4 shows a block diagram of a capsule-type endoscope controlling system according to the first embodiment.

FIG. 4 shows a block diagram of the capsule-type endoscope controlling system 90 according to the first embodiment. The capsule-type endoscope controlling system 90 includes the outside power source 60, the capsule-type endoscope 50 and the processor 70. The processor 70 includes a receiver 71, a processing circuit 72 and a display 73.

The receiver 71 receives the radio signal transmitted from the antenna 25 and demodulates the received signal to obtain the image signal and the attitude signal. The received signal is then outputted from the receiver 71 to the processing circuit 72. The processing circuit 72 performs image processing for the received image signal to generate a video signal of the internal body of the patient. The video signal is outputted to the display 73 to display the image (or a video picture). The attitude signal is also processed by the processing circuit 72 to indicate the attitude information on the display 73.

As shown in FIG. 4, the capsule-type endoscope 50 includes a combining circuit 27 which combines power from the coils 1-10 and supplies the combined power to the various components (the image sensor 22, the comparing circuit 21, etc.) of the capsule-type endoscope 50. It should be noted that in FIG. 4 only a part of the circuits in the capsule-type endoscope 50 is indicated for the sake of simplicity.

Hereafter, operation of the capsule-type endoscope controlling system 90 will be described in detail with reference to FIGS. 4-7.

First, the operation for detecting the attitude of the capsule-type endoscope 50 in the internal body of the patient will be explained. After the patient has swallowed the capsule-type endoscope 50, an operator turns on the power of the outside power source 60. Then, the outside power source 60 generates a time-varying magnetic field which oscillates in a direction M (a vertical direction) in FIGS. 5 and 6. The oscillation (i.e., the fluctuation of the amplitude of the magnetic field) is also illustrated in FIGS. 5 and 6 by a sine wave 63 indicated by a chain line.

By the change of the magnetic field, each of the coils 1-10 generates electromotive force. The power (i.e., the current) generated by the coils 1-10 is combined by the combining circuit 27 and then is supplied to the various components in the capsule-type endoscope 50.

Voltage values (i.e., electromotive forces) generated by the coils 1-10 are also inputted to the comparing circuit 21. In the comparing circuit 27, the orientations and distances of the coils 1-10 with respect to the outside power source 60 are calculated, so that the attitude of the capsule-type endoscope 50 is obtained.

Electromotive force of a coil changes depending on the magnetic flux density of the magnetic flux intersecting with the coil and an angle formed between the coil and the magnetic flux. Therefore, the output (i.e., the voltage value) of the coil (1-10) changes depending on an angle of an aperture surface of the coil with respect to the magnetic flux generated by the outside power source 60 and the distance from the outside power source 60.

Since, as described above, the coils 1-10 have the same electric characteristic, positional relationships between the coils 1-10 with respect to the outside power source 60 as well as angular relationships between the coils 1-10 with respect to the outside power source 60 can be detected based on the outputs of the coils 1-10.

More specifically, with regard to two coils which are positioned in parallel with each other and are located coaxially (e.g., two coils 1 and 2, two coils 3 and 7, two coils 5 and 9, and etc.), the output of one of the two coils closer to the outside power source 60 is larger than that of the other of the two coils. Therefore, the positional relationship between the two coils can be detected based on the outputs of the two coils.

When the coils 1 and 2 are positioned as indicated in FIG. 5, the output voltage B of the coil 1 is larger than the output voltage A of the coil 2. The reason is that the magnetic flux density reduces as the distance from the outside power source 60 increases, and that a distance DX between the outside power source 60 and the coil 1 is shorter than a distance DY between the outside power source 60 and the coil 2.

With regard to two coils which are adjacent to each other and are positioned perpendicularly with respect to each other (e.g., two coils 1 and 3, two coils 1 and 5, two coils 3 and 5, and etc.), the output voltage of one of the two coils is larger than that of the other of the two coils when an angle formed between the one of the two coils and a line L (see FIG. 6) is smaller than an angle formed between the other of the two coils and the line L. The reason is that the output voltage of the coil increases as the angle formed between the coil and the direction of the magnetic flux increases. In FIG. 6, the line L is perpendicular to the direction of the magnetic flux generated by the outside power source 60.

When the coils 1 and 3 are positioned as indicated in FIG. 6, an output voltage D of the coil 1 is larger than an output voltage C of the coil 3 because an angle β of the coil 1 with respect to the line L is smaller than an angle α of the coil 3 with respect to the line L. The angular relationship between the coils 1 and 3 with respect to the outside power source 60 is thus detected based on the output voltages C and D of the coils 1 and 3.

FIG. 7 shows a flow of operation for determining the attitude of the capsule-type endoscope 50 executed by the comparing circuit 21 of the capsule-type endoscope 50. In the following explanation, the side surfaces of the side board 20d of the printed circuit board 20 are defined as follows. The side surface on which the coils 3 and 4 are located is represented as a side surface SA1 (see FIG. 3). The side surface on which the coils 5 and 6 are located is represented as a side surface SA2. The side surface on which the coils 7 and 8 are located is represented as a side surface SA3. The side surface on which the coils 9 and 10 are located is represented as a side surface SA4.

In step S1, the outputs of the coils 1 and 2 are compared with each other to determine which is closer to the outside power source 60. In step S2, the sum of the outputs of the coils 3 and 4 on the side surface SA1 and the sum of the outputs of the coils 7 and 8 on the side surface SA3 are compared with each other to determine which of the side surfaces SA1 and SA3 is closer to the outside power source 60. In step S3, the sum of the outputs of the coils 5 and 6 on the side surface SA2 and the sum of the outputs of the coils 9 and 10 on the side surface SA4 are compared with each other to determine which of the side surfaces SA2 and SA4 is closer to the outside power source 60.

Then based on the results of the steps S1, S2 and S3, one apex of apexes of the rectangular prism shape of the printed circuit board 20 located closest to the outside power source 60 is determined (step S4).

Next, three coils surrounding and adjacent to the one apex closest to the outside power source 60 are selected. For example, if the one apex is an apex V1 (see FIG. 1), the selected three coils are the coils 1, 3 and 5. The outputs of the selected three coils are then compared with one another to determine the angular relationships among the selected three coils with respect to the line L (step S5).

In step S6, the attitude of the prismatic form of the capsule-type endoscope 50 with respect to the outside power source 60 is determined based on the result of the step S5. The attitude of the capsule-type endoscope 50 is then outputted from the comparing circuit 21 to the modulator 24 as the attitude signal. The attitude signal is modulated and amplified by the modulator 24, and then is transmitted via the antenna 25 as the radio signal.

The receiver 71 of the processor 70 receives the radio signal transmitted from the antenna 25 of the capsule-type endoscope 50, and demodulates the received radio signal to obtain the attitude signal. The attitude signal is then outputted from the receiver 71 to the processing circuit 72. The processing circuit 72 generates information indicating the attitude of the capsule-type endoscope 50. Then, the information indicating the attitude of the capsule-type endoscope 50 is displayed on the display 73.

The information indicating the attitude of the capsule-type endoscope 50 may be one of textual information and pictorial information. The information indicating the attitude of the capsule-type endoscope 50 may be superimposed on the observing image (video picture) of the internal body of the patient.

Hereafter, operation of the capsule-type endoscope controlling system 90 for observing the internal body of the patient will be explained.

When the power is generated by the coils 1-10 in the capsule-type endoscope 50 by the electromagnetic induction, the light source illuminates the object (the internal body of the patient) through the transparent cover 40a. Light reflected from the object is converged by the objective lens system 30a onto the image sensor 22.

The image picked up by the image sensor 22 is outputted from the image sensor 22 to the signal processing circuit 23 as the electric signal. As described above, the signal processing circuit 23 performs the predetermined process to generate the image signal. Then, the image signal is modulated and amplified by the modulator 24. Next, the image signal is transmitted through the antenna 25 as the radio signal.

The receiver 71 receives the radio signal transmitted from the antenna 25 of the capsule-type endoscope 50, and demodulates the received radio signal to obtain the image signal. The processing circuit 72 generates the video signal based on the image signal demodulated by the receiver 71. Then, the video image of the internal body of the patient is displayed on the display 73.

As described, according to the first embodiment of the invention, since the coils are located on all of the surfaces of the rectangular prism shape of the printed circuit board 20, the magnetic flux generated by the outside power source 60 intersects with at least two of the coils 1-10 regardless of the attitude of the capsule-type endoscope 50 in the internal body of the patient. Therefore, the capsule-type endoscope 50 can constantly and steadily generate the power (i.e., the electromotive force).

Further, according to the first embodiment of the invention, the attitude of the capsule-type endoscope 50 is obtained by utilizing a fact that the output voltage of the coil changes depending on the distance from the outside power source 60 and the angle of the coil with respect to the magnetic flux generated by the outside power source 60.

In the above mentioned embodiment, the printed circuit board 20 is formed by the flexible printed circuit board. However, the printed circuit board 20 may be formed by a combination of rigid printed circuit boards and flexible printed circuit boards.

Second Embodiment

Hereafter, a capsule-type endoscope 150 according to a second embodiment of the invention will be explained with reference to FIGS. 8-11. In FIGS. 8-11, as to elements which are similar to those of the first embodiment, the same reference numbers are assigned, and detailed explanations thereof will not be repeated. FIG. 8 is a perspective view of the capsule-type endoscope 150. Similarly to the first embodiment, the left side of the capsule-type endoscope 150 in FIG. 8 is defined as a front side, and a right side of the capsule-type endoscope 150 in FIG. 8 is defined as a rear side.

FIG. 9A is a side view of the capsule-type endoscope 150 viewed along an arrow A of FIG. 8. FIG. 9B is a side view of the capsule-type endoscope 150 viewed along an arrow B of FIG. 8. FIG. 9C is a front view of the capsule-type endoscope 150 viewed along an arrow C of FIG. 8. FIG. 10 is a developed view of a printed circuit board 120.

Similarly to the first embodiment, the capsule-type endoscope 150 is used together with the outside power source 60 and the processor 70. As shown in FIGS. 8-10, the feature of the second embodiment is that the number and shapes of coils (153, 155, 157, 159) located on each side surface of the side board 20d are different from those of the first embodiment.

The printed circuit board 120 includes the side board 20d having the four side surfaces on which coils 153, 155, 157 and 159 are located, respectively. The coils 153, 155, 157 and 159 have rectangular forms and have the same electrical characteristic. That is, the coils 153, 155, 157 and 159 generate the same output when they are in the same magnetic condition. The coils 153, 155, 157 and 159 correspond to a combination of the coils 3 and 4, a combination of the coils 5 and 6, a combination of the coils 7 and 8, and a combination of the coils 9 and 10, respectively.

It is understood that, similarly to the calculation process shown in FIG. 7 of the first embodiment, the attitude of the capsule-type endoscope 150 can be obtained. Since the size of each of the coils 153, 155, 157 and 159 is different from the size of each of the coils 1 and 2, the outputs of the coils 153, 155, 157 and 159 are adjusted in accordance with a difference of the electrical characteristic between each of the coils 1 and 2 and each of the coils 153, 155, 157 and 159.

More specifically, in this embodiment, the outputs of the coils 153 and 157 are compared with each other in step S2 of FIG. 7. In step S3 of FIG. 7, the outputs of the coils 155 and 159 are compared with each other. After the three coils (e.g., the coils 1, 155 and 157) surrounding one apex closest to the outside power source 60 is determined in step S4 of FIG. 7, the outputs of the selected three coils are compared with each other (in step S5 of FIG. 7). Then, the attitude of the prismatic form of the capsule-type endoscope 150 with respect to the outside power source 60 is determined based on the result of the step S5.

In addition to the above mentioned feature, the capsule-type endoscope 150 is capable of accommodating a rechargeable battery 160 (see FIG. 11). The power generated by the coils 1, 2, 153, 155, 157 and 159 is not only supplied to the various circuits in the capsule-type endoscope 150 but also supplied to the rechargeable battery 160 to accumulate power. When the power generated by the coils decreases, the power is supplied to the various circuits in the capsule-type endoscope 150 by the battery 160.

As shown in FIG. 10, on the rear circular board 20c, a spring 26 functioning as a negative terminal for the battery 160 is fixed. Further, on a bottom surface (not shown in FIG. 10) of the inside circular board 20b, a positive terminal (not shown) for the rechargeable battery 160 is formed. FIG. 11 shows a situation where the rechargeable battery 160 is accommodated in the capsule-type endoscope 150.

When the printed circuit board 120 is completely assembled and is mounted in the casing 40 as shown in FIG. 11, the rechargeable battery 160 is accommodated in space surrounded by the inside circular board 20b, the connecting board 20f and the rear circular board 20c. In this situation, the rechargeable battery 160 is pressed to the positive terminal of the bottom surface of the inside circular board 20b by the spring 26.

Since the rechargeable battery 160 is used to supply power when the power generated by the coils decreases, the power is supplied to the various circuits in the capsule-type endoscope 150 more steadily.

Third Embodiment

Hereafter, a capsule-type endoscope 250 according to a third embodiment of the invention will be described with reference to FIGS. 12-14. In FIGS. 12-14, as to elements which are similar to those of the first embodiment, the same reference numbers are assigned, and detailed explanations thereof will not be repeated. FIG. 12 is a perspective view of the capsule-type endoscope 250. Similarly to the first embodiment, the left side of the capsule-type endoscope 250 in FIG. 12 is defined as a front side, and a right side of the capsule-type endoscope 250 in FIG. 12 is defined as a rear side.

FIG. 13A is a side view of the capsule-type endoscope 250 viewed along an arrow A of FIG. 12. FIG. 13B is a side view of the capsule-type endoscope 250 viewed along an arrow B of FIG. 12. FIG. 13C is a front view of the capsule-type endoscope 250 viewed along an arrow C of FIG. 12. FIG. 14 is a developed view of a printed circuit board 220. Similarly to the first and second embodiments, the capsule-type endoscope 250 is used together with the outside power source 60 and the processor 70.

The feature of the capsule-type endoscope 250 is that printed circuit boards 201, 202, 203, 205, 207 and 209 having vortical patterns are used. The printed circuit boards 201, 202, 203, 205, 207 and 209 correspond to the coils 1, 2, 153, 155, 157 and 159 of the second embodiment. In this embodiment, the side board 20d is constituted by the printed circuit board 203, 205, 207 and 209, each of which has a rectangular form.

The printed circuit boards 203, 205, 207 and 209 form the side surfaces of the rectangular prism shape of the side board 20d. Similarly to the second embodiment, the vortical patterns formed on the printed circuit boards 201 and 202 have the same electrical characteristic. That is, the vortical patterns formed on the printed circuit boards 201 and 202 generate the same power (electromotive force) when they are in the same magnetic condition.

The vortical patterns formed on the printed circuit boards 203, 205, 207 and 209 have the same electrical characteristic. That is, the vortical patterns formed on the printed circuit boards 203, 205, 207 and 209 generate the same power (electromotive force) when they are in the same magnetic condition. Therefore, the attitude of the capsule-type endoscope 250 can be calculated by the same way as that described in the second embodiment.

Although the present invention has been described in considerable detail with reference to certain preferred embodiments thereof, other embodiments are possible.

Although in the above mentioned embodiments, the coils (or the vortical patterns) are located on all of the side surfaces of the rectangular prism shape of the side board 20d, substantially the same advantage as that of the above mentioned embodiments can also be attained by a configuration in which three coils (or three vortical patterns) are located on three of the side surfaces of the side board 20d. That is, the advantage can be attained by locating the three coils on three planes which are arranged to have different orientations.

FIG. 16 shows one of such configurations. In FIG. 16, only three coils 1, 3 and 5 are provided on the side board 20d. When a printed circuit board 320 is completely assembled and mounted in the casing 40, planes on which the coils 1, 3 and 5 are located perpendicularly intersect with each other.

In the above mentioned embodiments, the outside power source 60 generates the time-varying magnetic field. Such a time-varying magnetic field may be generated as an electromagnetic wave. The outside power source 60 may be configured to emit a microwave.

The coil or the vortical pattern may be made of metal. Alternatively, the coil or the vortical pattern may be made of conductive resin.

A loop antenna may be provided in the capsule-type device to generate power based on the time-varying magnetic field.

The capsule-type endoscope controlling system 90 may further include a magnetic field generating device 310 which generates a static magnetic field. FIG. 17A schematically shows the magnetic field generating device 310. As shown in FIG. 17A, the magnetic field generating device 310 has a north pole 311 and a south pole 312, which are located outside of the patient body so that a capsule-type endoscope 350 is located between the north pole 311 and the south pole 312.

FIG. 18 is a block diagram of the capsule-type endoscope 350. The capsule-type endoscope 350 has the same configuration as that of the capsule-type endoscope 50 of the first embodiment. The capsule-type endoscope 350 further has a receiver coil 355 and a detecting circuit 351 (see FIG. 18). The detecting circuit 351 is electrically connected to both end portions of the receiver coil 355. In FIGS. 17A and 17B, the receiver coil 355 is indicated as a cross section along a line I-I of FIG. 18.

The detecting circuit 351 detects a direction of current flowing through the receiver coil 355. When the magnetic field generating device 351 turns on the magnetic field, the current flows through the receiver coil 355 in directions as indicated in FIG. 17A. When the magnetic field generating device 351 turns off the magnetic field, the current flows through the receiver coil 355 in directions as indicated in FIG. 17B.

The detected result of the detecting circuit 351 is transmitted to the processor 70 through the modulator 24 and the antenna 25. By detecting the direction of the current flowing through the receiver coil 355 when the magnetic field is turned on or turned off, it becomes possible to determine whether the capsule-type endoscope 350 is overturned or not.

In the above mentioned embodiments, the outside power source 60 is configured to generate the time-varying magnetic field, and the capsule-type endoscope is configured to generate power by electromagnetic induction. However, the outside power source and the capsule-type endoscope may be configured to generate power by coupling of an electric field. In this case, the capsule-type device includes an electric field antenna such as a loop antenna.

FIG. 19 shows a capsule-type endoscope 450 configured to generate power by receiving a time-varying electric field. The capsule-type endoscope 450 has substantially the same configuration as that of the first, second or the third embodiment. Further, the capsule-type endoscope 450 has a loop antenna 451 to generate power in place of the coils. For example, the outside power source generates an electromagnetic wave 455 having an oscillating direction Y and a direction of travel X as indicated in FIG. 19. The loop antenna 451 receives the electromagnetic wave 455 to generate power.

One example of practical configurations of the loop antenna 451 is shown in FIG. 20. FIG. 20 shows an outward appearance of the capsule-type endoscope 450. On each side surface of the side board 20d, a plurality of loop antennas 451a arranged in a first direction and a plurality of loop antennas 451b arranged in a second direction perpendicular to the first direction are provided. With this structure, power is steadily generated by the loop antennas 451a and 451b regardless of the attitude of the capsule-type endoscope 450.

In the above mentioned second embodiment, the rechargeable battery (i.e., a secondary battery) 160 is used. However, a primary battery (e.g., a dry battery) may be used in place of the rechargeable battery 160 to supply power to the various circuits in the capsule-type endoscope.

The capsule-type endoscope may be configured such that the rechargeable battery 160 is used only if an emergency (e.g., breakdown of the outside power source 60) arises. Alternatively, the rechargeable battery 160 may be used to constantly supply power to the circuits in the capsule-type endoscope.

The display unit 73 may include two monitors which display the attitude information of the capsule-type endoscope and the observing image of the patient, respectively.

Although in the above mentioned embodiment, the capsule-type endoscope and the controlling system thereof are described by way of example, the present invention is also applied to various capsule-type devices for observing an internal body of a subject. In the above mentioned embodiment, the capsule-type device is configured to have an image sensor. Alternatively or additionally, the capsule-type device may have another sensor, such as a temperature sensor, used for obtaining information concerning the internal body of the subject. In this case, the information of the internal body of the subject is transmitted to the processor and is displayed on the display The capsule-type endoscope may be configured to transmit outputs of the coils without making the comparison among the outputs of the coils in the capsule-type endoscope. In this case, the outputs of the coils are transmitted to the processor, and the attitude of the capsule-type endoscope is calculated in the processor.

The present disclosure relates to the subject matter contained in Japanese Patent Application No. P2003-199243, filed on Jul. 18, 2003, which is expressly incorporated herein by reference in its entirety.

What is claimed is:

1. A capsule-type device, comprising:
   a power generator that generates power by receiving at least one of a time-varying electric field and a time-varying magnetic field;
   a casing that surrounds the power generator,
   the power generator including a plurality of receiving elements having different directionalities with regard to the at least one of the time-varying electric field and the time-varying magnetic field, the plurality of receiving elements having coils respectively located on planes having different orientations;
   an objective lens system that forms an image of an object, the coils including a coil located to cross an optical path of the objective lens system, the optical path passing through an opening of the coil;
   an image pickup device that converts the image formed thereon by the objective lens system to an image signal; and
   a transmitter that transmits the image signal, generated by the image pickup device, by a radio signal.

2. The capsule-type device according to claim 1, wherein the plurality of receiving elements are located on planes having different orientations.

3. The capsule-type device according to claim 1, wherein the plurality of receiving elements have the same electric and/or magnetic characteristic.

4. The capsule-type device according to claim 1, wherein the plurality of receiving elements are located on side surfaces of a rectangular prism shape.

5. The capsule-type device according to claim 4, further comprising:
a comparing system that makes a comparison among outputs of at least three receiving elements of the plurality of receiving elements so that an angular relationship between the at least three receiving elements and an outside power source that generates the at least one of the time-varying electric field and the time-varying magnetic field is detected, the at least three receiving elements being located perpendicularly to each other and being located adjacent to each other; wherein
the transmitter transmits a result of the comparison performed by the comparing system by a radio signal.

6. The capsule-type device according to claim 4, further comprising:
a comparing system that makes a comparison among outputs of at least two receiving elements of the plurality of receiving elements so that positional relationship between the at least two receiving elements and an outside power source that generates the at least one of the time-varying electric field and the time-varying magnetic field is detected, the at least two receiving elements being located parallel to each other and being located coaxially with respect to each other; wherein
the transmitter transmits a result of the comparison performed by the comparing system by a radio signal.

7. The capsule-type device according to claim 4, wherein the plurality of receiving elements are located on three of the side surfaces of the rectangular prism shape.

8. The capsule-type device according to claim 4, wherein the plurality of receiving elements are located on all of the side surfaces the rectangular prism shape.

9. The capsule-type device according to claim 1, further comprising:
a comparing system that makes a comparison among outputs of the plurality of receiving elements to determine an attitude of the capsule-type device; wherein
the transmitter transmits the determined attitude of the capsule-type device by a radio signal.

10. The capsule-type device according to claim 1, further comprising:
at least one sensor configured for obtaining information concerning an internal body of a subject when the capsule-type device is in the internal body of the subject; wherein
the transmitter transmits the information, obtained by the at least one sensor, by a radio signal.

11. The capsule-type device according to claim 1, wherein the coils are configured as vortical patterns on a printed circuit board.

12. The capsule-type device according to claim 1, further comprising a rechargeable battery configured to temporarily accumulate the power generated by the power generator.

13. The capsule-type device according to claim 1, wherein the plurality of receiving elements generate power by receiving a microwave.

14. A capsule-type device controlling system, comprising:
an outside power source that generates a time-varying magnetic field; and
a capsule-type device including a power generator that generates power by receiving the time-varying magnetic field to supply the power to internal components of the capsule-type device, the power generator including a plurality of coils located on at least three side surfaces of a rectangular prism shape, the plurality of coils being respectively located on planes having different orientations;
an objective lens system that forms an image of an object, the coils including a coil located to cross an optical path of the objective lens system, the optical path passing through an opening of the coil;
an image pickup device that converts the image formed thereon by the objective lens system to an image signal; and
a transmitter that transmits the image signal, generated by the image pickup device, by a radio signal.

15. The capsule-type device controlling system according to claim 14, further comprising a processor having a receiver that receives the radio signal transmitted by the transmitter of the capsule-type device, the processor determining an attitude of the capsule-type device with respect to the outside power source based on the received information.

16. The capsule-type device controlling system according to claim 14,
wherein the capsule-type device further includes:
a comparing system that makes a comparison among outputs of the plurality of coils to determine an attitude of the capsule-type device; wherein
the transmitter transmits the determined attitude of the capsule-type device by a radio signal.

17. The capsule-type device controlling system according to claim 14 further comprising,
a comparing system that makes a comparison among outputs of at least two coils of the plurality of coils so that positional relationship between the at least two coils and the outside power source that generates the time-varying magnetic field is detected, the at least two coils being located parallel to each other and being located coaxially with respect to each other; wherein
the transmitter transmits a result of the comparison performed by the comparing system by a radio signal.

18. The capsule-type device controlling system according to claim 14 further comprising,
at least one sensor configured for obtaining information concerning an internal body of a subject when the capsule-type device is in the internal body of the subject; wherein
the transmitter transmits the information, obtained by the at least one sensor, by a radio signal.

19. The capsule-type device controlling system according to claim 14, wherein the plurality of coils are configured as vortical patterns on a printed circuit board.

20. The capsule-type device controlling system according to claim 14 further comprising,
a rechargeable battery configured to temporarily accumulate the power generated by the power generator.

21. The capsule-type device controlling system according to claim 14, wherein the plurality of coils generate power by receiving a microwave.

* * * * *